United States Patent [19]
Osborn, III

[11] Patent Number: 4,738,676
[45] Date of Patent: Apr. 19, 1988

[54] PANTILINER

[75] Inventor: Thomas W. Osborn, III, Cincinnati, Ohio

[73] Assignee: The Procter & Gamble Company, Cincinnati, Ohio

[21] Appl. No.: 873,873

[22] Filed: Jun. 12, 1986

Related U.S. Application Data

[63] Continuation of Ser. No. 623,273, Jun. 21, 1984, abandoned, which is a continuation-in-part of Ser. No. 605,713, Apr. 30, 1984, abandoned.

[51] Int. Cl.⁴ .............................................. A61F 13/16
[52] U.S. Cl. .................... 604/385 R; 604/378
[58] Field of Search .................. 604/385.1, 366, 386, 604/369, 370, 390, 371, 372, 375, 378, 379

[56] References Cited

U.S. PATENT DOCUMENTS

| | | | |
|---|---|---|---|
| 3,105,491 | 10/1963 | Harwood | 604/375 |
| 3,229,691 | 1/1966 | Crowe | 604/371 |
| 3,371,667 | 4/1968 | Morse | 604/369 |
| 3,973,567 | 10/1976 | Stinivasan | 604/385 R |
| 3,987,792 | 10/1976 | Hernandez | 604/372 |
| 4,023,571 | 5/1977 | Comerford et al. | 604/385 R |
| 4,200,103 | 4/1980 | Black et al. | 604/370 |
| 4,219,024 | 8/1980 | Patience | 604/366 |
| 4,275,105 | 6/1981 | Boyd | 604/366 |
| 4,397,644 | 8/1983 | Matthews et al. | 604/378 |
| 4,405,326 | 9/1983 | Lenaghan | 604/385 R |

Primary Examiner—John D. Yasko
Attorney, Agent, or Firm—J. M. Pollaro; F. H. Braun; R. C. Witte

[57] ABSTRACT

A pantiliner consisting essentially of an overwrap and a resilient element. The overwrap is a soft, smooth, compliant, porous material while the resilient element is compressible, conformable, and resilient. The former can be any material commonly used as a topsheet for sanitary napkins while the latter is preferably a mass of moisture insensitive fibers which can be bonded one to another at their points of contact. Preferably, the surfaces of the fibers are hydrophilic. Adhesive attachment means are preferably associated with the pantiliner.

5 Claims, 2 Drawing Sheets

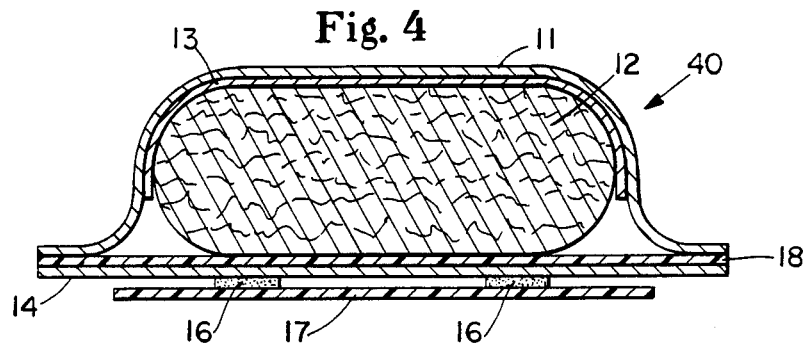
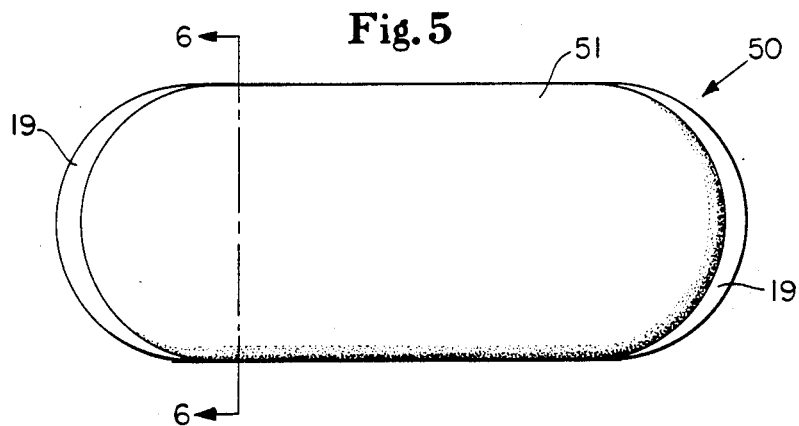
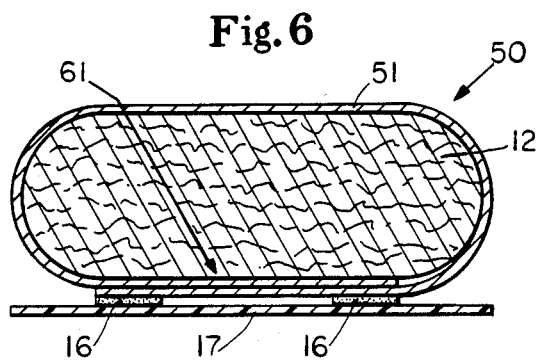

PANTILINER

CROSS REFERENCE TO RELATED APPLICATION

This is continuation of application Ser. No. 06/623,273, filed on June 21, 1984, abandoned, which is a continuation-in-part of application Ser. No. 605,713, filed Apr. 30, 1984, Abandoned.

BACKGROUND OF THE INVENTION

1. Field of the Invention

This invention relates to an absorbent device which is a species of sanitary napkin commonly denominated a pantiliner.

2. Background Art

Sanitary napkins are used by women principally during their menstrual periods to receive and contain menses and other vaginal discharges to protect their garments from soiling. While early versions of sanitary napkins required the use of various specialized belts and supporters, modern designs provide for the adhesive attachment of the sanitary napkin directly to the crotch region of the user's undergarment, normally her panty. Modern sanitary napkins can be efficient and effective at accomplishing their intended purposes.

Many women in modern society have developed the habit of wearing an absorbent device between their menstrual periods to protect their clothing from any small quantity of vaginal discharges then present. Sanitary napkins are frequently used for this purpose. While such use is efficient, conventional sanitary napkins are usually rather bulky (because they are designed to contain relatively large volumes of fluid) and their use is less comfortable to the wearer than the use of an undergarment along.

Devices which are less bulky, and consequently more comfortable to use, than conventional sanitary napkins have appeared in the consumer market. These devices are usually intended to be affixed to the crotch region of the user's undergarment during times between her menstrual periods, during times when menstrual flow is light, and as supplemental protection for other catamenial products. They have, because of their use and relatively small size, been called pantiliners or, in some literature, panty liners.

Frequently, pantiliners are scaled down versions of conventional sanitary napkins. The present invention departs from this practice by providing a unique, exemplary device designed specifically to be a pantiliner.

Morse, in U.S. Pat. No. 3,371,667 issued Mar. 5, 1968, describes a sanitary napkin comprising a conventional wrapper, a "functional, highly porous resilient element immediately adjacent the surface of the absorbent product which is to be placed against the body and which element serves to entrap highly viscous, mucoid and gelatinous constituents of the body fluids," and a "highly absorbent, relatively dense core." The resilient element is of low density and can comprise synthetic fibers such as polyamides and polyesters. It is said to be essential that these fibers be stablized. The interstitial walls of the low density web are rendered hydrophilic by treatment with a wetting agent.

Harwood et al, in U.S. Pat. No. 3,029,817 issued Apr. 17, 1962, describe a sanitary napkin comprising an absorbent core or batt and a control element. The batt is "of a conventional highly absorbent material of the type used for absorbent bandages," and the control element "preferably consists of fluid repellent fibers such as synthetic fibers, but certain other fibers which to some extent are wetable may be employed." It is preferred that the fibers in the control element "range in length from about one inch upwardly."

SUMMARY OF THE INVENTION

The present invention is of a pantiliner comprising a porous overwrap and a resilient element. Optionally, and preferably, the pantiliner also comprises adhesive attachment means with an associated release liner. Optionally, the pantiliner includes a liquid barrier.

BRIEF DESCRIPTION OF THE DRAWINGS

FIG. 4 is a cross sectional view of still another embodiment of a pantiliner of this invention as if taken along line 2—2 of FIG. 1.

FIG. 5 is a plan view of an alternate embodiment of the pantiliner of this invention.

FIG. 6 is a cross sectional view of the pantiliner shown in FIG. 5 taken along line 6—6 of FIG. 5.

Figure 1:
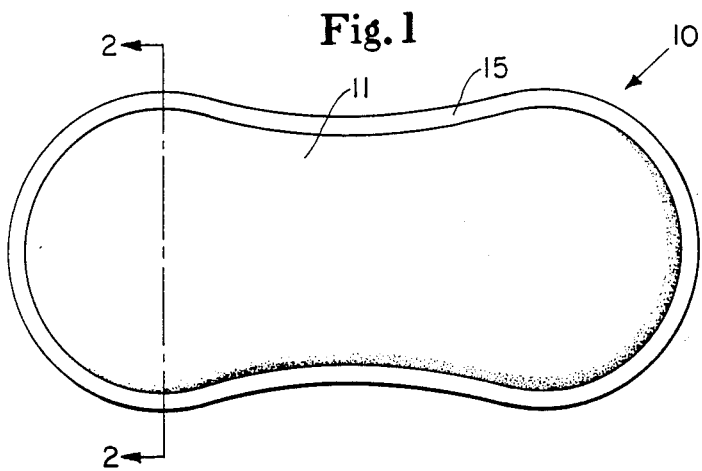
FIG. 1 is a plan view of a pantiliner of this invention.

In the drawings the thicknesses of certain materials have been exaggerated for clarity. In the various figures, reference numerals are used consistently to refer to identical or equivalent elements.

DETAILED DESCRIPTION OF THE INVENTION

While this specification concludes with claims particularly pointing out and distinctly claiming that which is regarded as the invention, it is believed that the invention can be more readily understood through perusal of the following detailed description of the invention in conjunction with study of the associated drawings. While the present invention is described in terms of particular embodiments, it is to be understood that various designs can be used and are considered to be within the scope of the invention so long as the devices employ the necessary components having the characteristics and properties described infra.

Figure 2:
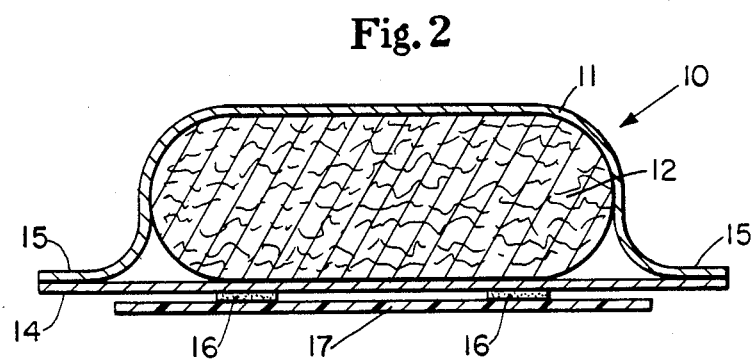
FIG. 2 is a cross sectional view of the pantiliner shown in FIG. 1 taken along line 2—2 of FIG. 1.

A preferred embodiment of the present invention, pantiliner 10, is shown in plan view in FIG. 1 and in cross sectional view in FIG. 2. Pantiliner 10 consists of the two necessary components: an overwrap (exemplified by top overwrap 11 and a bottom overwrap 14) and resilient element 12.

In FIG. 2 the overwrap is shown in two sections, top overwrap 11 and bottom overwrap 14, rather than as a single section because of the ease of constucting pantiliner 10 when the overwrap is in two parts. It is to be understood that the precise number of sections joined to form the overwrap is immaterial. In fact, an overwrap constructed of a single section of material is illustrated and discussed infra.

The overwrap is any soft, smooth, compliant, porous material which will be comfortable against human skin and through which vaginal discharges will tend to pass. Those skilled in the art can readily select woven and non-woven materials useful for this purpose. In general, porous materials used as topsheets for disposable diapers or as coverings for conventional sanitary napkins can be used in the present invention.

Preferred overwraps include formed thermoplastic films such as those described with the particularity in U.S. Pat. No. 4,324,246 issued to Mulane and Smith on Apr. 13, 1982 as well as in U.S. Pat. No. 4,342,314 issued to Radel and Thompson on Aug. 3, 1982. Useful overwraps are also described in U.S. Pat. No. 4,341,217 issued to Ferguson and Landrigan on July 27, 1982. The three patents just mentioned are incorporated herein by reference.

It is possible to manufacture a pantiliner following the teachings of this invention, but without an overwrap; such a construction is not preferred, however.

The second necessary component of the present invention is the resilient element indicated by reference numeral 12 in FIG. 2. The resilient element must be compressible, conformable, and resilient. That is to say, the resilient element must possess such physical properties that forces applied to it by the action of the body of the pantiliner user will readily cause the resilient element to bend and to compress and to conform to the space available for it as the pantiliner is held adjacent the user's body.

Preferably, the resilient element comprises a mass or batt of fibers. While the resilient element can comprise other materials, such as a synthetic foam material, such use is less preferred than the use of a fibrous batt.

The resilient element must be resilient. That is to say, it must, without the application of external forces, return to essentially its original size and shape after deforming forces are removed. Preferably, the resilient element possesses such resilience that it will recover at least about 80% of its original volume after it is compressed to about 20% of its original volume and the compressing forces are removed. Its resilience must be essentially unaffected by the presence of moisture such as the moisture in vaginal discharges; that is to say, the resilient element must be essentially moisture insensitive.

The resilient element must be of relatively low density so that it has sufficient void volume to contain practical quantities of vaginal discharges. Low density can also help to insure that the resilient element is readily deformable under the influence of the user's body thereby exhibiting comfort attributes. Preferably, the density of the resilient element is from about 0.01 to about 0.1 gram per cubic centimeter.

The surfaces of the interstices of the resilient element must be hydrophilic. More generally, the resilient element must comprise a material which is wetted by the fluids in question. Vaginal discharges and other bodily fluids are primarily aqueous solutions and suspensions; surfaces which are wetted by these fluids can be broadly described as hydrophilic. As used in this specification, the term "hydrophilic" describes surfaces which are wetted by the fluid in question. Thus, the resilient element must be hydrophilic.

The state of the art respecting wetting of materials allows definition of hydrophilicity (and wetting) in terms of contact angles and the surface tensions of the fluids and solids involved. This is discussed in detail in The American Chemical Society publication entitled *Contact Angle, Wetability, And Adhesion* edited by Robert F. Gould, and coyprighted in 1964, which publication is incorporated herein by reference. A surface is said to be wetted by a fluid either when the contact angle between the fluid and the surface is less than 90° or when the fluid will tend to spread spontaneously across the surface; both conditions normally coexist.

Vaginal discharges normally have a surface tension of from about 35 to about 60 dynes per centimeter. They will have contact angles of less than 90° and will tend to spread spontaneously across a solid surface which has a critical surface tension value greater than the fluid surface tension. Since the surface tension of water is normally higher than that of vaginal discharges, any solid which is wetted by water (i.e. which is literally hydrophilic in the precise, limited meaning of the word) is also usually wetted by vaginal discharges.

The materials used in the resilient element can achieve hydrophilicity by any convenient means. For example, the material itself can be intrinsically hydrophilic, although, as discussed infra, this circumstance is relatively rare for materials useful in the resilient element. The surfaces of the resilient element can be rendered hydrophilic by treatment with a surfactant, such as a nonionic or an anionic surfactant, as by spraying the material with a surfactant or dipping the material into the surfactant.

A resilient element possessing the requisite properties can be obtained most readily through the use of a batt of synthetic fibers; preferably the fibers are bonded one to another at a significant number of their points of contact.

Synthetic fibers useful in the present invention include those made of cellulose acetate, polyvinyl chloride, polyvinylidene chloride, acrylic resins, polyvinyl acetates, non-soluble polyvinyl alcohols, polyethylenes, polypropylenes, polyamides, and, preferably, polyesters. Preferred polyester fibers have a denier of from about 4 to about 15 and a length of from about 2 to about 8 centimeters.

As indicated supra, resiliency of the resilient element can frequently be enhanced if the fibers are bonded together at their points of contact. Thermal bonding can be used or, preferably, adhesives, such as latex adhesives, can be used to bond the synthetic fibers one to another.

As discussed supra, the surfaces of the interstices of the resilient element, and, in turn, the surfaces of the fibers, must be hydrophilic. Hydrophilicity can be achieved by selecting fibers which are inherently hydrophilic. The problem with achieving hydrophilicity by this method is that hydrophilic fibers, such as rayon, generally lose thier resiliency in the presence of moisture. Preferably, then, synthetic fibers such as polyester are used and are treated with surfactant as discussed supra to render the surfaces hydrophilic.

Suitable surfactants include nonionic surfactants such as Brij 76 manufactured by ICI Americas, Inc. of Wilmington, Del. and the various materials sold under the Pegosperse trademark by Glyco Chemicals, Inc. of Greenwich, Conn. Anionic surfactants can also be used. Surfactants are applied to the fibers at a level of from about 0.2 to about 1 gram per square meter of resilient element.

Synthetic foams useful as the resilient elemement include polyester foam materials (such as those described by DesMarais in U.S. Pat. No. 4,110,276 issued Aug. 29, 1978 and incorporated herein by reference), polyurethane foams, styrene-butadiene foams, and cellulose sponge material. The synthetic foam should be soft and flexible, open celled, and of medium cell size. Its interior surfaces should be hydrophilic. Incorporation of surfactant during foam manufacture or addition of surfactant to the preformed foam are two suitable methods of insuring that the interior surfaces are hydrophilic. The foam should have a density of from about 0.1 to about 0.8 grams per cubic centimeter. The use of an overwrap with a synthetic foam resilient element can be optional.

Referring again to FIGS. 1 and 2 which illustrate a preferred embodiment of the present invention, top overwrap 11 and bottom overwrap 14 are placed on either side of resilient element 12 and are sealed about the periphery of pantiliner 10 with seal 15. Seal 15 can be achieved by mechanical crimping, thermal welding, ultrasonic welding, use of adhesive, etc.

In the embodiment illustrated in FIG. 2, pantiliner 10 is provided with optional adhesive fastening means 16. In FIG. 2 adhesive fastening means 16 are illustrated as two narrow strips running essentially the entire length of pantiliner 10. This arrangement is selected for convenience; those skilled in the art can readily select a different pattern for the adhesive attachment means.

The purpose of the adhesive attachment means is, of course, to secure the pantiliner in the crotch of the user's undergarment. Any adhesive or glue used with sanitary napkins for such purposes can be used with this invention. Pressure sensitive adhesives are preferred. Suitable adhesives include Century A-305IV are manufactured by Century Adhesive Corporation and Instant Lok 34-2823 manufactured by National Starch Company.

Other means for physically securing the pantiliner in the crotch region of the user's undergarment can be used, but adhesive attachment means are preferred.

When adhesive attachment means 16 is present in the device, it is usually covered, prior to the time the user affixes the pantiliner to her undergarment, with release liner 17. Release liner 17 serves to keep adhesive attachment means 16 from drying out and to keep it from sticking to extraneous surfaces prior to use. Any release liner commonly used for such purposes with sanitary napkins can be used with this invention. Non-limiting examples of suitable release liners are BL30MG-A SILOX E1-0 and BL30MG-A SILOX 4P/O manufactured by Akrosil Corporation.

Figure 3:
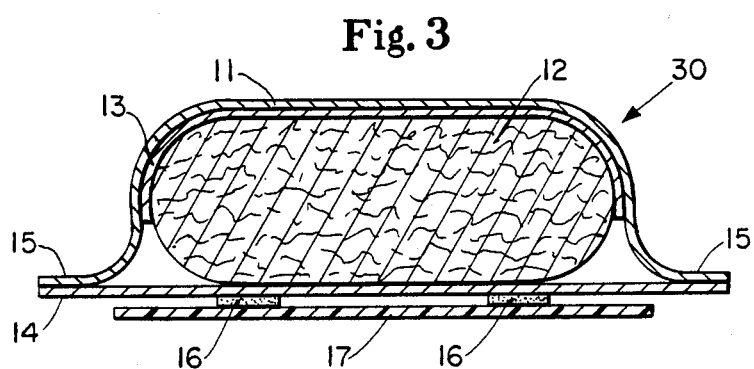
FIG. 3 is a cross sectional view of an alternate embodiment of a pantiliner of this invention as if taken along line 2—2 of FIG. 1.

An alternate, and especially preferred, embodiment of the present invention is illustrated as pantiliner 30 in FIG. 3. Pantiliner 30 has the same plan form as pantiliner 10 illustrated in FIG. 1, but it has the cross section taken along line 2—2 as illustrated in FIG. 3. The differnce between the embodiments illustrated in FIGS. 2 and 3 is the presence of wicking layer 13 interposed between overwrap 11 and resilient element 12 in pantiliner 30. Any material which causes vaginal discharges contacting the surface of pantiliner 30 to migrate along and across the under surface of top overwrap 11 thereby tending to distribute the vaginal discharges across the whole of the pantiliner can be used. One suitable technique is the provision of a layer of fibers affixed to the inner surface of the overwrap as described in the previously incorporated patent to Mulane and Smith. Preferably, wicking layer 13 comprises a sheet of tissue paper closely associated with the inner surface of top overwrap 11. Tissue papers used in commonly available facial tissue products, such as that marketed under the registered trademark PUFFS by The Procter & Gamble Company of Cincinnati, Ohio can be used. Especially preferred are tissue papers manufactured by either of the processes discribed in U.S. Pat. No. 3,301,746 issued to Sanford and Sisson on Jan. 31, 1967 and U.S. Pat. No. 3,994,771 issued to Morgan and Rich on Nov. 30, 1976. Both of these two patents are incorporated herein by reference.

FIG. 4 illustrates a second alternate embodiment of the present invention, pantiliner 40. Pantiliner 40 has the same plan form as pantiliner 10 illustrated in FIG. 1, but it has the cross section taken along line 2—2 as illustrated in FIG. 4. Pantiliner 40 differs from pantiliner 30 in that it possesses an optional liquid barrier 18 interposed between resilient element 12 and bottom overwrap 14. (An alternate positioning of liquid barrier 18 is on the opposite surface of bottom overwrap 14 so that bottom overwrap 14 is interposed between liquid barrier 18 and resilient element 12.) In general, a liquid barrier is not needed in the pantiliner of the present invention because of the relatively small volume of vaginal discharge the device is intended to absorb. The absence of a liquid barrier allows the pantiliner to be that much smaller, less bulky, softer, more flexible, and compressible. Those skilled in the art, however, can readily select materials for liquid barrier 18 which do not significantly detract from the comfort of the present invention. Suitable materials include, for example, polyethylene film having a thickness of from about 0.25 to about 1.0 millimeter. Woven and nonwoven fabrics which have been treated to render them liquid repellant can also be used. Breathable, liquid resistant materials, and as those described in U.S. Pat. No. 3,881,489 issued to Hartwell on May 6, 1975 and U.S. Pat. No. 3,989,867 issued to Sisson on Nov. 2, 1976 can also be used. These two patent are incorporated herein by reference.

A still further embodiment of the present invention is illustrated in FIGS. 5 and 6. Pantiliner 50 has, in plan form, generally linear longitudinal edges and rounded ends while pantiliners 10, 30 and 40 are of hourglass shape with rounded ends. Construction of pantiliner 50 with essentially linear longitudinal edges allows the optional use of a single section of overwrap material as overwrap 51. Overwrap 51 passes completely about resilient element 12 and overlaps it at the rear of pantiliner 50 in the vicinity of region 61. Overwrap 51 is secured to itself in vicintiy of region 61 by securement means (not shown) such as adhesive attachment. Overwrap 51 is also secured to itself at the distal ends of pantiliner 50 along end seals 19 by any conventient means such as adhesive attachment.

Preferably, the pantiliner of this invention is of hourglass shape as illustrated by pantiliner 10 in FIG. 1. The size of pantiliner 10 can be conveniently selected by those skilled in the art. Typically, pantiliner 10 is from about 5 to about 8 centimeters wide at its widest point and is from about 3 to about 5 centimeters wide at its narrowest point. Typically, pantiliner 10 is from about 12 to about 16 centimeters from distal end to distal end. It is typically from about 0.3 to about 6 centimeters thick in its uncompressed state.

The absorbent capacit of resilient element 12, on an absolute basis, has been found to be not particularly critical. Obviuosuly, a more absorbent resilient element would be preferred to a less absorbent resilient element provided the compressibility and the resilience of the two were equal. Compressibility and resilience, which directly affect the perceived comfort of the device by the user, are, then, more important in the design and construction of the present invention than is the absolute absorbent capacity of the resilient element.

EXAMPLE

A pantiliner having the planform illustrated in FIG. 1 and the cross-sectional configuration illustrated in FIG. 3 is constructed. The top overwrap and the bottom overwrap are both formed thermoplastic films as described above. The resilient element is a latex-bonded polyester manufactured by Pellon Corporation and sold under the Pellon trademark; it is about 0.4 centimeter thick (uncompressed) and weighs about 1.4 grams. The overwraps are sealed one to the other by ultrasonic welding. The wicking layer comprise a single sheet of PUFFS tissues as described above. The pantiliner is about 14.7 centimeters long, about 6.6 centimeters wide at its widest point, and about 5.6 centimeters wide at its narrowest point. Adhesive attachment means comprising two longitudinal strips of Century A-3051V adhesive covered by BL3MG-A SICOX E1-0 release liner are used. In use, the pantiliner is found to be comfortable to wear, and it effectively and efficiently absorbs small amounts of vaginal discharge.

What is claimed is:

1. A sanitary napkin comprising a means for containing vaginal discharges consisting solely of a rersilient element of a relatively low density, compressible, conformable and resilient batt of synthetic fibers having interstices to provide sufficient void volume to contain practical quantities of vaginal discharges, the surfaces of said fibers being hydrophilic so as to rapidly contain the vaginal discharges and said fibers being bonded on to another at a significant number of their points of intersection, said resilient element possessing a resilience such that it will recover at least about 80% of its original volume after it is released from a compression force that reduces its volume to about 20% of its original volume, the resilience being essentially unaffected by the presence of moisture; and a porous overwrap enclosing said means for containing vaginal discharges.

2. The sanitary napkin of claim 1 wherein said sanitary napkin includes an additional component comprising a wicking layer interposed between said overwrap and said resilient element.

3. The sanitary napkin of claims 1 or 2 wherein said overwrap comprises a non-woven fabric.

4. The sanitary napkin of claims 1 or 2 wherein said overwrap comprise a formed thermoplastic film 5. The sanitary napkin of claim 1 which includes as an additional element a liquid impervious sheet interposed between said resilient element and said porous overwrap.

* * * * *

UNITED STATES PATENT AND TRADEMARK OFFICE
CERTIFICATE OF CORRECTION

PATENT NO. : 4,738,676

DATED : April 19, 1988

INVENTOR(S) : Thomas W. Osborn, III

It is certified that error appears in the above-identified patent and that said Letters Patent is hereby corrected as shown below:

Column 1, line 6, delete "This is continuation" and insert --This is a continuation--

Column 1, line 36, delete "along" and insert --alone--

Column 4, line 60, delete "elemement" and insert --element--

Column 5, line 46, delete "pantilner" and insert --pantiliner--

Column 5, line 48, delete "differnce" and insert --difference--

Column 5, line 67, delete "discribed" and insert --described--

Column 6, line 32, delete "patent" and insert --patents--

Column 6, line 43, delete "vicintiy" and insert --vicinity--

Column 6, line 46, delete "conventient" and insert --convenient--

Column 6, line 58, delete "capacit" and insert --capacity--

Column 6, line 60, delete "Obvisously" and insert --Obviously--

Column 7, line 12, delete "comprise" and insert --comprises--

Column 7, line 24, delete "rersilient" and insert --resilient--

UNITED STATES PATENT AND TRADEMARK OFFICE
CERTIFICATE OF CORRECTION

PATENT NO. : 4,738,676

DATED : April 19, 1988

INVENTOR(S) : Thomas W. Osborn, III

It is certified that error appears in the above-identified patent and that said Letters Patent is hereby corrected as shown below:

Column 8, line 4,        delete "on" and insert --one--

Column 8, line 21,       delete "comprise" and insert --comprises--

Signed and Sealed this

Twenty-third Day of August, 1988

Attest:

DONALD J. QUIGG

Attesting Officer    Commissioner of Patents and Trademarks